United States Patent
Song

(10) Patent No.: US 10,168,282 B2
(45) Date of Patent: Jan. 1, 2019

(54) FAST METHOD FOR BATCH SCREENING DIAMONDS

(71) Applicant: GUANGZHOU BIAOQI OPTOELECTRONICS TECHNOLOGY DEVELOPMENT CO., LTD., Guangzhou, Guangdong (CN)

(72) Inventor: Guangjun Song, Guangdong (CN)

(73) Assignee: GUANGZHOU BIAOQI OPTOELECTRONICS TECHNOLOGY DEVELOPMENT CO., LTD., Guangzhou (CN)

( * ) Notice: Subject to any disclaimer, the term of this patent is extended or adjusted under 35 U.S.C. 154(b) by 0 days.

(21) Appl. No.: 15/546,015

(22) PCT Filed: May 6, 2016

(86) PCT No.: PCT/CN2016/000246
§ 371 (c)(1),
(2) Date: Jul. 25, 2017

(87) PCT Pub. No.: WO2017/113429
PCT Pub. Date: Jul. 6, 2017

(65) Prior Publication Data
US 2018/0003633 A1    Jan. 4, 2018

(30) Foreign Application Priority Data
Dec. 27, 2015 (CN) .......................... 2015 1 1009698

(51) Int. Cl.
*G01N 21/00* (2006.01)
*G01N 21/64* (2006.01)
(Continued)

(52) U.S. Cl.
CPC ............. *G01N 21/64* (2013.01); *C30B 29/04* (2013.01); *G01N 21/6456* (2013.01); *G01N 21/87* (2013.01); *G01N 21/8806* (2013.01)

(58) Field of Classification Search
CPC ........ G01N 21/64; G01N 21/87; G01N 21/88; G01N 21/65; G01N 33/38; C03B 29/04
See application file for complete search history.

(56) References Cited

U.S. PATENT DOCUMENTS

2007/0036921 A1* 2/2007 Twitchen ............... A44C 17/00
                                                                  428/15
2010/0326138 A1* 12/2010 Kumatani .......... B23K 26/0676
                                                                  65/286
2012/0170019 A1    7/2012 Linares et al.

FOREIGN PATENT DOCUMENTS

CN       105352929 A     2/2016
WO    2015007873 A1     1/2015

OTHER PUBLICATIONS

General Administration of Quality Supervision, Inspection and Quarantine, Kimberley Process Certification Scheme and Rough Diamond Inspection, ISBN 7-5066-3936-X, Jul. 31, 2006, pp. 159-160, Standards Press of China, Beijing, China.

(Continued)

*Primary Examiner* — Abdullahi Nur

(57) ABSTRACT

A fast method for batch screening diamonds includes placing diamonds on a worktable, turning on a light source arranged on one side of the worktable to shed light on the diamonds where the light includes visible light, photographing the diamonds on the worktable through an imager to obtain a basal image showing the distribution of the diamonds, switching the light source to shortwave UV light with a wavelength ranging from 180 nm to 250 nm, maintaining the light source in work condition for a period of time and then turn it off, photographing the diamonds on the (Continued)

worktable through the imager to obtain a phosphorescence distribution image showing phosphorescent diamonds, overlapping the basal image with the phosphorescence distribution image to obtain a phosphorescence comparison map, marking the phosphorescent diamonds on the phosphorescence comparison map through image recognition technology, and then picking out the phosphorescent diamonds as suspicious diamonds.

5 Claims, 1 Drawing Sheet

(51) Int. Cl.
  *C30B 29/04* (2006.01)
  *G01N 21/87* (2006.01)
  *G01N 21/88* (2006.01)

(56) References Cited

OTHER PUBLICATIONS

International Search Report of PCT Patent Application No. PCT/CN2016/000246 dated Jul. 7, 2016.

\* cited by examiner

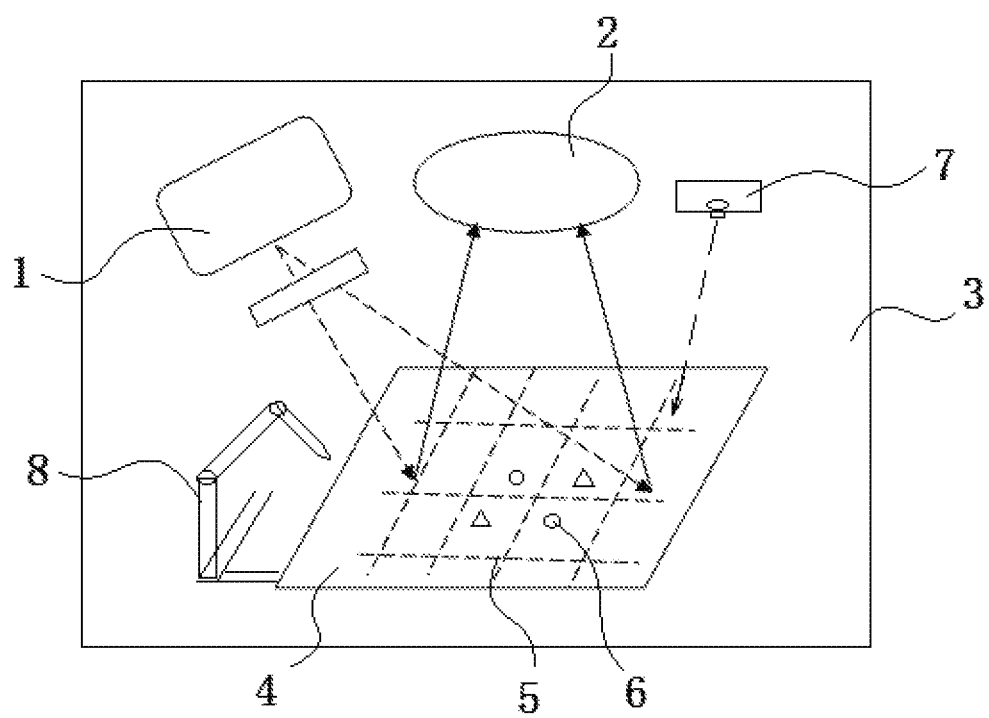

FAST METHOD FOR BATCH SCREENING DIAMONDS

FIELD OF THE INVENTION

The present invention relates to the field of detection instruments, and to be more specific, it relates to a fast method for batch screening diamonds.

BACKGROUND OF THE INVENTION

Diamonds fluoresce during exposure to ultraviolet light (UV light). Some diamonds normally present blue fluorescence under UV light while a few present yellow fluorescence.

In addition to the property of exhibiting fluorescence, some diamonds phosphoresce. Diamond fluorescence is the phenomenon when diamonds are exposed to UV light and present blue fluorescence at different intensities. Diamonds phosphorescence is the light emission of diamonds after the UV light is turned off.

Since different diamonds present various colors of fluorescence at various intensities, the simplest method for preliminary detection on large quantities of diamonds is exposing them under UV light. If the diamonds fluoresce different colors at different intensities, they are natural diamonds; if, however, the fluorescence emitted by the diamonds presents the same color at the same intensity, it is probably that the diamonds are synthetic diamonds.

In recent years, synthetic diamonds have been mixed into natural diamonds for sell by illegal businessmen. Conventional diamond detection methods are slow for screening large quantities of synthetic diamonds and natural diamonds. Moreover, the equipments and detection methods are normally designed for detecting big size diamonds but of no use when fast screening of melee diamonds (very small diamonds) is in need. Normally, diamond dealers purchase large amount of melee diamonds and thus spend a lot of time on conventional diamond detection without reducing the risk of purchasing synthetic diamonds.

SUMMARY OF THE INVENTION

The present invention aims at providing a fast method, which is of low cost but with high efficiency, for batch screening diamonds.

In order to realize the above-mentioned goal, the present invention provides a fast method for batch screening diamonds, wherein the fast method for batch screening diamonds is implemented using a light source (1), an imager (2), a worktable (4) and a darkroom (3) housing the light source (1), the imager (2) and the worktable (4), and the fast method for batch screening diamonds comprises a first step comprising placing diamonds (6) on the worktable (4), turning on the light source (1) arranged on one side of the worktable (4) to shed light on the diamonds (6) where the light includes visible light, and photographing the diamonds (6) on the worktable (4) through the imager (2) to obtain a basal image showing the distribution of the diamonds (6);

a second step comprising switching the light source (1) to shortwave UV light with a wavelength ranging from 180 nm to 250 nm, maintaining the light source (1) in work condition for a period of time and then turn it off, and photographing the diamonds (6) on the worktable (4) through the imager (2) to obtain a phosphorescence distribution image showing phosphorescent diamonds; and a third step comprising overlapping the basal image with the phosphorescence distribution image to obtain a phosphorescence comparison map, marking the phosphorescent diamonds on the phosphorescence comparison map through image recognition technology, and then picking out the phosphorescent diamonds as suspicious diamonds manually or using a device.

Preferably, the second step further comprises switching the light source (1) to shortwave UV light with a wavelength ranging from 180 nm to 250 nm, maintaining the light source (1) in work condition, photographing the diamonds (6) on the worktable (4) through the imager (2) to obtain a fluorescence distribution map showing fluorescent diamonds, overlapping the basal image with the fluorescence distribution image to obtain a fluorescence comparison map, and marking the fluorescent diamonds on the fluorescence comparison map.

Preferably, the worktable (4) is set with a grid (5) having cells each printed with symbols and numbers, the phosphorescence comparison map in the third step contains the grid (5).

Preferably, the worktable (4) is provided with an auxiliary positioning device (7) which is able to emit a beam of visible light on where the suspicious diamonds locate, such that the suspicious diamond can be picked out manually.

Preferably, the worktable (4) is further provided with a manipulator (8) which is able to pick out the suspicious diamonds in the light of the phosphorescence comparison map.

The present invention further provides an instrument for fast batch screening of diamonds, wherein the instrument comprises a light source (1), an imager (2), a worktable (4), a darkroom (3) housing the light source (1), the imager (2) and the worktable (4); the light source (1) is located above one side of the worktable (4); the imager (2) is arranged above the worktable (4); the light source (1) comprises a shortwave UV light module and a visible light module.

Preferably, the light source (1) is a xenon lamp, a deuterium lamp, a LED light with a wavelength ranging from 180 nm to 250 nm, or a laser light with a wavelength ranging from 180 nm to 250 nm.

Preferably, the imager (2) is a digital camera, a film camera or a video camera.

Preferably, the worktable (4) is provided with a grid (5).

Preferably, the worktable (4) is further provided with an auxiliary positioning device (7) or a manipulator (8).

The present screening method is fast as it collects the phosphorescence comparison map of diamonds and capable of screening and detecting a batch of diamonds simultaneously to largely enhance the screening and detection efficiency and lower the cost. Furthermore, the present screening method is widely applicable to fast detection of diamonds in different states and different shapes, for example loose diamonds, mounted diamonds, or even diamonds weigh as minimum as 0.001 carats. An additional use of the fluorescence comparison map in the present screening method further improves the screening and detection accuracy rate.

BRIEF DESCRIPTION OF THE DRAWINGS

The Figure is a schematic view of a detection instrument capable of fast batch screening of diamonds of the present invention.

DETAILED DESCRIPTION OF ILLUSTRATED EMBODIMENTS

Embodiments of the present invention are further explained clearly as follows in conjunction with figures.

As shown in the Figure, a fast method for batch screening diamonds by means of a light source 1, an imager 2, a worktable 4 and a darkroom 3 housing the light source 1, the imager 2 and the worktable 4 comprises the following steps.

The first step comprises placing diamonds 6 on the worktable 4, turning on the light source 1 arranged on one side of the worktable 4 to shed light on the diamonds 6 where the light includes visible light, photographing the diamonds 6 on the worktable 4 through the imager 2 to obtain a basal image showing the distribution of the diamonds 6.

The second step comprises switching the light source 1 to shortwave UV light with a wavelength ranging from 180 nm to 250 nm, maintaining the light source 1 in work condition for a period of time and then turn it off, photographing the diamonds 6 on the worktable 4 through the imager 2 to obtain a phosphorescence distribution image showing phosphorescent diamonds. Phosphorescence of diamonds is the light emission of diamonds after removing UV light. The phosphorescence emission of diamonds is readily to be recorded using the imager 2 after turning off the UV light in the present step. The imager 2 could also record the duration and the intensity of the phosphorescence emission, identify which could enhance the accuracy of the screening and detection of diamonds. The power of the shortwave UV light is about 25 watts. The UV light is turned on for 1 second. Since the duration of phosphorescence ranges from 1 second to 60 seconds, photographing should be done within the this time frame.

The third step comprises overlapping the basal image with the phosphorescence distribution image to obtain a phosphorescence comparison map, marking the phosphorescent diamonds on the phosphorescence comparison map through image recognition technology, and then picking out the phosphorescent diamonds as suspicious diamonds manually or using a device. Usually diamonds that phosphoresce blue-green are high-temperature high-pressure (HTHP) diamonds and thus can be identified as synthetic diamonds.

In order to obtain a fluorescence distribution map, the light source 1 used in the second step includes a shortwave UV light with a wavelength ranging from 180 nm to 250 nm. The second step further comprises maintaining the light source 1 in work condition, photographing the diamonds 6 on the worktable 4 through the imager 2 to obtain a fluorescence distribution map showing fluorescent diamonds, overlapping the basal image with the fluorescence distribution image to obtain a fluorescence comparison map, and marking the fluorescent diamonds on the fluorescence comparison map. Shortwave UV light plays a supplementary role in appraising the quality and authenticity of diamonds by means of the fluorescence distribution map.

In order to easily identify the location of the suspicious diamonds, the worktable 4 is set with a grid 5 having cells each printed with symbols and numbers. The phosphorescence comparison map in the third step contains the grid 5. Therefore, by means of computer analysis which identifies the numbers printed in the cells in which the phosphorescent diamonds located and relative locations of the phosphorescent diamonds in the cells, synthetic diamonds that phosphoresce blue-green can be speedily marked on the phosphorescence comparison map.

In order to easily conduct manual screening and avoid misoperation, the worktable 4 is provided with an auxiliary positioning device 7, which is able to emit a beam of visible light on where the suspicious diamonds locate, thus the suspicious diamond can be picked out manually. By means of the auxiliary positioning device 7, it is very convenient for an operator to identify and pick out the suspicious diamonds.

In order to easily conduct automatic screening, the worktable 4 is further provided with a manipulator 8, which is able to pick out the suspicious diamonds in the light of the phosphorescence comparison map. The manipulator 8 is able to move its way above the phosphorescent diamonds and pick out the suspicious diamonds.

The present invention further provides an instrument which is capable of fast batch screening of diamonds, comprising a light source 1, an imager 2, a worktable 4, a darkroom 3 housing the light source 1, the imager 2 and the worktable 4. The light source 1 is located above one side of the worktable 4. The imager 2 is arranged above the worktable 4. The light source 1 comprises a shortwave UV light module and a visible light module.

In order to provide stable shortwave UV light, the light source 1 is a xenon lamp, a deuterium lamp, a LED light with a wavelength ranging from 180 nm to 250 nm or a laser light with a wavelength ranging from 180 nm to 250 nm. If xenon lamp or deuterium lamp are adopted, a filter may be provided in front of both lamps to obtain shortwave UV light since both lamps could emit not only UV light but also visible light.

In order to obtain a better image, the imager 2 is a digital camera, a film camera or a video camera.

In order for a better distribution of the diamonds, the worktable 4 is provided with a grid 5.

In order to carry out an easy screening of diamonds, the worktable 4 is further provided with an auxiliary positioning device 7 and/or a manipulator 8. Through the use of the auxiliary positioning device 7 which is able to emit a beam of visible light on where the suspicious diamonds locate, an operator could easily identify and pick out the suspicious diamonds. The manipulator 8 is able to move its way above the phosphorescent diamonds and pick out the suspicious diamonds.

The present screening method is fast as it collects the phosphorescence comparison map of diamonds and capable of screening and detecting a batch of diamonds simultaneously to largely enhance the screening and detection efficiency and lower the cost. Furthermore, the present screening method is widely applicable to fast detection of diamonds in different states and different shapes, for example loose diamonds, mounted diamonds, or even diamonds weigh as minimum as 0.001 carats. An additional use of the fluorescence comparison map in the present screening method further improves the screening and detection accuracy rate.

The above-mentioned embodiments are the preferred embodiments of the present invention and are considered in all respects as illustrative and not restrictive. Variations and modifications are allowed within the scope of the invention. Those skilled in the art will appreciate that the features described above can be combined in various ways to form multiple variations of the invention. As a result, such variations fall within the scope of the protection to the present invention.

What is claimed is:

1. A fast method for batch screening diamonds, characterized in that the fast method for batch screening diamonds is implemented using a light source (1), an imager (2), a worktable (4) and a darkroom (3) housing the light source (1), the imager (2) and the worktable (4), and the fast method for batch screening diamonds comprises a first step comprising placing diamonds (6) on the worktable (4), turning on the light source (1) arranged on one side of the worktable (4) to shed light on the diamonds (6) where the light includes visible light, and photographing the diamonds (6) on the worktable (4) through the imager (2) to obtain a basal image showing the distribution of the diamonds (6);

a second step comprising switching the light source (1) to shortwave UV light with a wavelength ranging from 180 nm to 250 nm, maintaining the light source (1) in work condition for a period of time and then turn it off, and photographing the diamonds (6) on the worktable (4) through the imager (2) to obtain a phosphorescence distribution image showing phosphorescent diamonds; and a third step comprising overlapping the basal image with the phosphorescence distribution image to obtain a phosphorescence comparison map, marking the phosphorescent diamonds on the phosphorescence comparison map through image recognition technology, and then picking out the phosphorescent diamonds as suspicious diamonds manually or using a device.

2. The fast method for batch screening diamonds according to claim 1, characterized in that the second step further comprises switching the light source (1) to shortwave UV light with a wavelength ranging from 180 nm to 250 nm, maintaining the light source (1) in work condition, photographing the diamonds (6) on the worktable (4) through the imager (2) to obtain a fluorescence distribution map showing fluorescent diamonds, overlapping the basal image with the fluorescence distribution image to obtain a fluorescence comparison map, and marking the fluorescent diamonds on the fluorescence comparison map.

3. The fast method for batch screening diamonds according to claim 1, characterized in that the worktable (4) is set with a grid (5) having cells each printed with symbols and numbers, the phosphorescence comparison map in the third step contains the grid (5).

4. The fast method for batch screening diamonds according to claim 1, characterized in that the worktable (4) is provided with an auxiliary positioning device (7) which is able to emit a beam of visible light on where the suspicious diamonds locate, such that the suspicious diamond can be picked out manually.

5. The fast method for batch screening diamonds according to claim 1, characterized in that the worktable (4) is further provided with a manipulator (8) which is able to pick out the suspicious diamonds in the light of the phosphorescence comparison map.

\* \* \* \* \*